United States Patent [19]

Springmann et al.

[11] 4,310,473
[45] Jan. 12, 1982

[54] PROCESS FOR SEPARATING SULFURIC ACID FROM SULFOXIDATION OUTPUT

[75] Inventors: Hermann Springmann, Haltern; Karl Borchers, Borken, both of Fed. Rep. of Germany

[73] Assignee: Chemische Werke Hüls AG, Marl, Fed. Rep. of Germany

[21] Appl. No.: 240,251

[22] Filed: Mar. 3, 1981

[30] Foreign Application Priority Data

Apr. 10, 1980 [DE] Fed. Rep. of Germany ....... 3013808

[51] Int. Cl.³ ...................... C07C 143/02; C07B 13/00
[52] U.S. Cl. ................................. 260/504 S; 210/708
[58] Field of Search ............. 210/634, 643, 648, 708, 210/727, 728; 260/504 S, 513 R

[56] References Cited

U.S. PATENT DOCUMENTS

| | | | |
|---|---|---|---|
| 2,263,041 | 11/1941 | Lazar | 260/504 S |
| 2,368,452 | 1/1945 | Dawson | 260/504 S |
| 2,479,202 | 8/1949 | Bransky | 260/504 S |
| 3,927,081 | 12/1975 | Thomas | 260/504 S |
| 4,119,661 | 10/1978 | Balakirev | 260/513 R |
| 4,177,208 | 12/1979 | Boy et al. | 260/504 S |
| 4,178,307 | 12/1979 | Boy et al. | 260/504 S |
| 4,233,236 | 11/1980 | Keen | 260/504 S |

FOREIGN PATENT DOCUMENTS

| | | | |
|---|---|---|---|
| F 3718 | 1/1953 | Fed. Rep. of Germany | 260/504 S |
| 2139477 | 2/1972 | Fed. Rep. of Germany | 260/504 S |
| 2065477 | 10/1973 | Fed. Rep. of Germany | 210/504 S |
| 2745691 | 10/1977 | Fed. Rep. of Germany | 260/504 S |
| 1478530 | 4/1967 | France | 260/504 S |
| 1179743 | 1/1970 | United Kingdom | 210/708 |

*Primary Examiner*—Ernest G. Therkorn
*Attorney, Agent, or Firm*—Wells & Wells

[57] ABSTRACT

The process for separating sulfuric acid from the sulfoxidation output obtained when paraffins are reacted with sulfuric acid, oxygen and water in the presence of ultraviolet light, using an alcohol containing at least 5 C atoms, is improved by treating the sulfoxidation output with a 0.25 to 2.5 fold amount by weight of a mixture of (a) 40 to 95% by weight of alcohol, and
(b) 5 to 60% by weight of paraffins and the aqueous phase formed thereby is separated with the sulfuric acid.

4 Claims, No Drawings

PROCESS FOR SEPARATING SULFURIC ACID FROM SULFOXIDATION OUTPUT

BACKGROUND OF THE INVENTION

The field of the invention is the after treatment of the sulfonation products of non-aromatic hydrocarbon mixtures and the state of the art may be ascertained by reference to U.S. Pat. Nos. 4,177,208 and 4,178,307; French Pat. No. 1,478,530 and West German Patent Application No. F 3718.120, 32/01 of Roderich Graf, Hans Gruschke and Kurt Schimmelschmidt, published Jan. 29, 1953, the disclosures of which are incorporated herein.

The term "sulfoxidation method" is widely used for the process where sulfur dioxide and oxygen are made to act simultaneously on n-paraffins possibly bearing functional groups or on cycloparaffins to produce paraffin sulfonic acids.

The practically implementable process variables differ first of all by the kind of initiation of the sulfoxidation. Among these known initiation means are ultraviolet light, the ozone method and the gamma-ray process, and processes involving the addition of peroxide compounds. There are furthermore the methods employing acetic acid anhydride, light-water and chlorine as disclosed in CHEMIE IN UNSERER ZEIT, 13, 1979, pp. 157.

As regards the light-water sulfoxidation process, that is, the process where paraffins are reacted with sulfur dioxide, oxygen and water in the presence of ultraviolet light: in addition to the paraffin sulfonic acids desired, also sulfuric acid must be removed in the course of the processing of the sulfoxidation output. The term sulfoxidation output, also within the scope of the present invention, defines the reaction output which is degassed and already freed from most of the unconverted paraffin.

According to the state of the art, the sulfuric acid is removed by treating the sulfoxidation output with an organic solvent in order to induce demixing into an organic phase containing the totality of the paraffin sulfonic acids and into an aqueous phase containing the sulfuric acid as much as possible in the form of a solution which is generally 15 to 25% by weight sulfuric acid. Thereupon the two phases are separated and the organic phase is further processed to isolate the paraffin sulfonic acids or their salts.

This German patent application No. F 3718.120, 32/01 discloses as useful organic solvents benzene, chlorobenzene, cyclohexane, carbon tetrachloride, chloroform, methylene chloride, 1,2-dichloroethane, tetrahydrofuran and the alcohol butanol.

French Pat. No. 14 78 530 discloses the use of quite generally oxygen containing organic compounds such as alcohols, ethers and ketones as organic solvents. Amyl alcohol is especially emphasized from among the groups of alcohols.

As shown by U.S. Pat. No. 4,178,307, which discloses the use of ethers, ketones, esters and (cyclo)-aliphatic ketoesters in columns 2 and 3 as organic solvents, difficulties may arise when alcohols having at least 5 C atoms are used in the continuous process mode as disclosed in U.S. Pat. No. 4,177,208, because following the recovery of the alcohol used it was not sufficiently freed from its sulfonated paraffins.

It is known that aliphatic and cycloaliphatic alcohols having at least 5 C atoms in the molecule can be used as extractants to extract the organic components from a crude sulfonation mixture containing unreacted paraffin, water and sulfuric acid besides the desired sulfonic acids, as disclosed in U.S. Pat. No. 4,177,208. In the process, the sulfuric acid separates in the aqueous phase and thus it can be isolated from the alcohol extract. The unreacted paraffin present together with the sulfonic acids remains in the lighter weight organic phase. The entire amount of paraffin present then is separated after neutralization of the sulfonic acids and removal of the extractant from the sulfonic acids present in the form of alkali sulfonates in a further process stage. This process of U.S. Pat. No. 4,177,208 includes the following steps:

(a) admixing with the paraffin sulfonic acid solution, at least one slightly polar alcohol selected from the group consisting of aliphatic and cycloaliphatic alcohols containing at least 5 carbon atoms, having a solubility in water less than 7% by weight which forms an azeotrope with water, thereby forming a mixture having an organic phase containing paraffin sulfonic acids dissolved therein and an aqueous phase containing the sulfuric acid;

(b) separating the organic phase from the aqueous phase;

(c) neutralizing the separated organic phase by admixture with a composition selected from the group consisting of alkali metal hydroxides, alkali metal carbonates, alkaline earth metal oxides, alkaline earth metal hydroxides, and alkaline earth metal carbonates thereby converting the sulfonic acids present in the organic phase into sulfonates, and forming a neutralized organic phase wherein the ratio of the amount of water to the amount of slightly polar alcohol in the neutralized phase is at most equal to the corresponding ratio for the azeotrope which forms between water and the slightly polar alcohol; and (d) removing the volatile components from the neutralized organic phase to recover the sulfonates under temperature and pressure conditions whereby the sulfonates are in a molten state.

SUMMARY OF THE INVENTION

Having in mind the limitations of the prior art, it is an object of the present invention to provide a light-water process which uses alcohols having at least 5 C atoms during the separation of sulfuric acid without the need for costly isolating operations during the recovery of the input materials.

Another object of the present invention is to improve the separation behavior where the separation behavior is measured by dwell time in the separator and the degree of separation of the sulfuric acid present.

Still another object of the present invention is an improvement over the process disclosed in U.S. Pat. No. 4,177,208.

According to the present invention, paraffins are reacted with sulfuric acid, oxygen and water in the presence of ultraviolet light and after degassing the sulfoxidation output includes paraffin sulfonic acids, sulfuric acid, water and non-sulfonated paraffins. The concentration of non-sulfonated paraffins is about 20 to 40% by weight. The sulfoxidation output is then treated with about 0.25 to 2.5 fold amount by weight of a mixture of:

(a) 40 to 95% by weight of an alcohol having at least 5 carbon atoms; and (b) 5 to 60% by weight of paraffin to form an organic phase containing paraffin sulfonic acids and an aqueous phase containing the sulfuric acid. The aqueous phase containing the sulfuric acid is then separated.

It could not be expected from the teaching of U.S. Pat. No. 4,177,208 that by adding given amounts of paraffin, the already good separation behavior of alcohols with at least 5 C atoms could be improved further.

DESCRIPTION OF THE PREFERRED EMBODIMENTS

The process of the present invention is implemented so that the total weight of sulfoxidation output is reacted with an amount by weight of the mixture of (a) alcohol and (b) paraffin which is ¼ to 2½, preferably 0.5 to 1.75 times the total weight of sulfoxidation output. The reaction takes place at a temperature of 10° to 60° C., preferably 20°–45° C. for a given time. The given time is easily ascertained by trial and error but generally ranges between 10 to 60 minutes.

The mixture consisting of (a) and (b) contains 40 to 95% by weight, preferably 70 to 85% by weight of alcohol and 5 to 60% by weight, preferably 15 to 30% by weight of paraffin.

The alkanols and cycloalkanols suitable as solvents for the process of the present invention have 5 to 12, preferably 6 to 9 C atoms. Representative alkanols and cycloalkanols are pentanol-1, hexanol-1, heptanol-1, octanol-1, nonanol-1, decanol-1, dodecanol-1,2-ethylbutanol-1, 2-methylpentanol, 2-ethylhexanol-1, 2,6-dimethyl-4-heptanol, 3-ethylhexanol-1,2,7-dimethyloctanol, octanol-2 and cyclohexanol. Obviously other mixtures of alcohols may also be used. In the process of the present invention, 2-ethylhexanol-1, heptanol-1, octanol-1 and nonanol-1 are preferred.

Basically all those paraffins are suitable that can be used in sulfoxidation. Preferably, however, n-paraffins having 7 to 30 C atoms are preferred, and especially those having 10 to 20 C atoms.

As a rule the paraffins used for the phase separation are identical with the paraffins used in the sulfoxidation, or at least extensively so. A less than full identity for instance may be due to the composition of the paraffin blends changing during the sulfoxidation process.

After the treatment, that is, following the thorough mixing of the sulfoxidation output with the mixture of alcohol and paraffin, which can be carried out in any commercial agitating unit, for instance a stirring vessel, a dwell time ensues for the formation of the two phases, which are then separated. This separation can be both continuous and discontinuous.

The processing of the organic phase can be carried out in various ways and the processing depends upon the product desired. It depends most of all on whether free paraffin sulfonic acids are desired, or paraffin sulfonates, preferably alkali sulfonates.

To obtain the free paraffin sulfonic acids, the alcohol is removed, and the paraffin also, for instance by azeotropic distillation at a pressure at most equal to atmospheric. The amount of water in the alcohol-paraffin solution of the paraffin sulfonic acids is controlled so that all of the alcohol and paraffin in the azeotropic mixture is distilled off together with the water. The paraffin sulfonic acids are obtained in the form of a liquid at the bottom of the column, and this liquid is neutralized, where appropriate, for the conversion into sulfonates.

The procedure for separating the paraffin sulfonic acids in the form of sulfonates is such that before the separation of alcohol and paraffin, the organic phase is treated with a basic compound. Suitable basic compounds are hydroxides and carbonates of the alkali metals, preferably of sodium and potassium, also oxides, hydroxides and carbonates of the alkali earth metals, preferably of calcium. Sodium hydroxide is especially preferred as a basic compound and hence as a neutralizer.

The basic compounds are useful in solid form or as aqueous solutions and in proportions at least sufficient to neutralize the total amount of the paraffin sulfonic acids. Preferably, quantities slightly exceeding the stoichiometric proportions are used, for instance up to 1.2 Val of the basic compound per Val of paraffin sulfonic acid.

The salts of the paraffin sulfonic acids then are freed from the organic phase so treated such as disclosed in U.S. Pat. No. 4,177,208, for instance by means of a thin film evaporator, i.e., from the extractant, namely the mixture of alcohol, paraffin and the water. The paraffin sulfonates are withdrawn as a melt from the evaporator sump. The head product obtained is a mixture of alcohol, paraffin and water, which is separated into an organic and an aqueous phase.

When required, the organic phase of alcohol and paraffin thereupon is freed from paraffin to the extent that a mixture remains in the composition and required concentration which can again be added to another sulfoxidation output for the purpose of phase separation. The separated paraffin appropriately is returned into the sulfoxidation process.

The products, free paraffinic sulfonic acids or their alkali or earth alkali salts produced or isolated by the present process are mainly used in detergent formulations.

All percentage data, including the examples and comparison tests below, which illustrate the process of the present invention, are by weight unless otherwise stated.

All examples and comparison tests start from a sulfoxidation output of the following percentage composition:

| paraffin sulfonic acids | 22.0 |
| paraffins (non-sulfonated) | 30.0 |
| water | 39.6 |
| sulfuric acid | 7.4 |

The paraffin mixture used for the sulfoxidation and as paraffin component (b) was of the following composition:

| $C_{number}$ | % by weight |
| --- | --- |
| $C_{12}$ | 1.07 |
| $C_{13}$ | 9.49 |
| $C_{14}$ | 27.8 |
| $C_{15}$ | 28.1 |
| $C_{16}$ | 19.8 |
| $C_{17}$ | 10.2 |
| $C_{18}$ | 3.04 |
| $C_{19}$ | 0.5 |

EXAMPLES 1 THROUGH 7 AND COMPARISON TEST A

In each example, 200 g of the sulfoxidation output of the above compositions were reacted with the amounts listed in Column 2 of Table 1 of 2-ethylhexanol-(1) (Comparison Test A), i.e., with a defined mixture of 2-ethylhexanol-(1) (a) and paraffin (b). The mixture was thoroughly stirred at 25° C. and placed in a settling vessel for separation. Upon the elapsed dwell time listed in Column 4 of Table 1, the aqueous phase was separated for the first time (I), after 30 minutes for the second time (II) and after 24 hours for the third time (III). The degree of separation of the sulfuric acid referred to that sulfuric acid present in the sulfoxidation output is listed in the relevant columns of Table 1.

EXAMPLES 8 THROUGH 14 AND COMPARISON TEST B

Examples 1 through 7 and Comparison Test A were repeated except that the mixing of the sulfoxidation output with (a) or (a) and (b) was carried out at 40° C. rather than at 25° C. Table 2 shows the results.

COMPARISON TEST C 200 g of the sulfoxidation output listed above were reacted with 250 g of 2-ethylhexanol-(1) and thoroughly mixed at 25° C. After 30 minutes, it was possible to separate 84.6 g of the lower aqueous phase with a content of 16.3% of sulfuric acid. This amounts to a calculated sulfuric acid separation degree of 93.2%. This value must be contrasted with the separation of 95.7% in Example 3 of Table 1.

COMPARISON TEST D

Comparison test C was repeated, except that the sulfoxidation output was treated at 40° C. After 30 minutes, 87.1 g of lower aqueous phase with a content of 16.3% of sulfuric acid were separated. This results in a sulfuric acid separation of 95.9%. This value must be contrasted with the 99.6% separation in Example 10 of Table 2.

TABLE 1

| | | | I | | II | | III | |
|---|---|---|---|---|---|---|---|---|
| Comparison Test | Amount of a, or a + b gm | Proportion of b in a + b % by weight | Dwell Times min. | Amount of Separated Lower Phase gm | Dwell Times min. | Amount of Separated Lower Phase gm | Dwell Times hr. | Amount of Separated Lower Phase gm |
| A | 200 | 0 | 12 | 64.7 | 30 | 10.5 | 24 | 4 |
| Example | | | | | | | | |
| 1 | 210.5 | 5 | 10 | 75.7 | 30 | 6.6 | 24 | 2.5 |
| 2 | 222.2 | 10 | 9 | 77.1 | 30 | 5.9 | 24 | 2.6 |
| 3 | 250 | 20 | 5 | 80.2 | 30 | 4.1 | 24 | 1.5 |
| 4 | 285.7 | 30 | 6 | 74.2 | 30 | 7.8 | 24 | 3.1 |
| 5 | 333.3 | 40 | 6 | 78.2 | 30 | 5.4 | 24 | 2.5 |
| 6 | 400 | 50 | 5.5 | 75.9 | 30 | 7.7 | 24 | 2.8 |
| 7 | 500 | 60 | 6 | 76.8 | 30 | 7.5 | 24 | 3 |

| Comparison Test | Total Amount of Lower Phases [ΣI − III] gm | Proportion of $H_2SO_4$ in [ΣI − III] % by weight | Separated $H_2SO_4$ Referred to amount of $H_2SO_4$ in Output % by weight | | |
|---|---|---|---|---|---|
| | | | I | I + II | I + II + III |
| A | 79.2 | 16.9 | 77.3 | 85.9 | 90.4 |
| Example | | | | | |
| 1 | 84.8 | 16.5 | 84.4 | 91.7 | 94.5 |
| 2 | 85.6 | 16.8 | 87.5 | 94.2 | 97.2 |
| 3 | 85.8 | 16.8 | 91 | 95.7 | 97.4 |
| 4 | 85.1 | 17 | 85.2 | 95.3 | 97.8 |
| 5 | 86.1 | 17.1 | 90.4 | 96.6 | 99.5 |
| 6 | 86.4 | 16.9 | 86.7 | 95.5 | 98.7 |
| 7 | 87.3 | 16.8 | 87.2 | 95.7 | 99.1 |

TABLE 2

| | | | I | | II | | III | |
|---|---|---|---|---|---|---|---|---|
| Comparison Test | Amount of a, or a + b gm | Proportion of b in a + b % by weight | Dwell Times min. | Amount of Separated Lower Phase gm | Dwell Times min. | Amount of Separated Lower Phase gm | Dwell Times hr. | Amount of Separated Lower Phase gm |
| B | 200 | 0 | 4 | 78.3 | 30 | 7.6 | 24 | 1.2 |
| Example | | | | | | | | |
| 8 | 210.5 | 5 | 4.3 | 83 | 30 | 4.6 | 24 | 1.7 |
| 9 | 222.2 | 10 | 3.9 | 79.8 | 30 | 7.3 | 24 | 1.4 |
| 10 | 250 | 20 | 2.9 | 84.8 | 30 | 5.6 | 24 | 0.7 |
| 11 | 285.7 | 30 | 4.2 | 84.4 | 30 | 4.4 | 24 | 1.1 |
| 12 | 333.3 | 40 | 2.8 | 82.8 | 30 | 6.8 | 24 | 1.1 |
| 13 | 400 | 50 | 2.8 | 82.5 | 30 | 8.2 | 24 | 0.8 |
| 14 | 500 | 60 | 3.3 | 79.1 | 30 | 10.3 | 24 | 1.3 |

| Comparison Test | Total Amount of Lower Phases [ΣI − III] gm | Proportion of $H_2SO_4$ in [ΣI − III] % by weight | Separated $H_2SO_4$ Referred to amount of $H_2SO_4$ in Output % by weight | | |
|---|---|---|---|---|---|
| | | | I | I + II | I + II + III |

TABLE 2-continued

| | B | 87.1 | 16.2 | 85.7 | 94 | 95.3 |
|---|---|---|---|---|---|---|
| Example | | | | | | |
| 8 | | 89.3 | 16.4 | 92 | 97 | 99.0 |
| 9 | | 88.5 | 16.3 | 87.9 | 95.9 | 97.5 |
| 10 | | 91.1 | 16.3 | 93.4 | 99.6 | 100.0 |
| 11 | | 89.9 | 16.2 | 92.4 | 97.2 | 98.4 |
| 12 | | 90.7 | 16.1 | 90.1 | 97.5 | 98.7 |
| 13 | | 91.5 | 15.9 | 88.6 | 97.4 | 98.3 |
| 14 | | 90.7 | 16.0 | 85.5 | 96.6 | 98.1 |

We claim:

1. A process for separating sulfuric acid from a sulfoxidation product containing in addition to said sulfuric acid, paraffin sulfonic acids, water and non-sulfonated paraffins, which comprises:
(A) admixing with the sulfoxidation product in a ratio of about 0.25 to 2.5 parts by weight of a mixture consisting essentially of:
(a) about 40 to 95% by weight of at least one slightly polar alcohol selected from the group consisting of aliphatic and cycloaliphatic alcohols having at least 5 carbon atoms and having a solubility in water less than 7% by weight which forms an azeotrope with water; and
(b) about 5 to 60% by weight of second paraffins having 7 to 30 carbon atoms in addition to said non-sulfonated paraffins
and thereby forming an aqueous phase containing said sulfuric acid and an organic phase containing said paraffin sulfonic acids and said paraffins; and
(B) separating said aqueous phase from said organic phase.

2. The process of claim 1, wherein said mixture consists of
(a) 70 to 85% by weight of said polar alcohol; and
(b) 15 to 30% by weight of said second paraffins.

3. The process of claim 2, wherein said polar alcohol has 5 to 12 C atoms.

4. The process of claim 3, wherein said polar alcohol has 6 to 9 C atoms, and said second paraffins have 10 to 20 C atoms.

* * * * *